(12) United States Patent
Govari

(10) Patent No.: US 6,400,981 B1
(45) Date of Patent: Jun. 4, 2002

(54) RAPID MAPPING OF ELECTRICAL ACTIVITY IN THE HEART

(75) Inventor: Assaf Govari, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 198 days.

(21) Appl. No.: 09/598,862

(22) Filed: Jun. 21, 2000

(51) Int. Cl.$^7$ ................................................. A61B 5/04
(52) U.S. Cl. ....................................................... 600/509
(58) Field of Search ................................. 600/508, 509, 600/510

(56) References Cited

U.S. PATENT DOCUMENTS

| | | | |
|---|---|---|---|
| 4,649,924 A | 3/1987 | Taccardi | 128/642 |
| 5,297,549 A | 3/1994 | Beatty et al. | 128/642 |
| 5,311,866 A | 5/1994 | Kagan et al. | 128/642 |
| 5,385,146 A | 1/1995 | Goldreyer | 128/642 |
| 5,391,199 A | 2/1995 | Ben-Haim | 607/122 |
| 5,443,489 A | 8/1995 | Ben-Haim | 607/115 |
| 5,450,846 A | 9/1995 | Goldreyer | 128/642 |
| 5,471,982 A | 12/1995 | Edwards et al. | 128/642 |
| 5,487,391 A | 1/1996 | Panescu | 128/699 |

(List continued on next page.)

FOREIGN PATENT DOCUMENTS

| | | | |
|---|---|---|---|
| EP | 0 661 948 B1 | 11/1997 | A61B/5/042 |
| EP | 0 900 547 A1 | 3/1999 | A61B/17/36 |
| EP | 0 900 548 A1 | 3/1999 | A61B/17/36 |
| EP | 0 974 936 A2 | 1/2000 | G06T/17/20 |
| WO | WO 94/04938 | 3/1994 | A61B/5/06 |
| WO | WO 94/06349 | 3/1994 | A61B/5/042 |
| WO | WO 96/05768 | 2/1996 | A61B/5/06 |
| WO | WO 97/24981 | 7/1997 | A61B/5/0215 |
| WO | WO 97/25917 | 7/1997 | A61B/5/04 |
| WO | WO 98/43530 | 10/1998 | A61B/1/00 |
| WO | WO 99/06112 | 2/1999 | A61N/1/04 |

OTHER PUBLICATIONS

Michael Kass, Andrew Witkin and Demetri Terzopoulos; Snakes: Active Contour Models; Proceedings of First International Conference Vision, 1987 pp. 259–268.

Demetri Terzopoulos; Regularization of Inverse Visual Problems Involving Discontinuities; IEEE Transactions on Pattern Analysis and Machine Intelligence, vol. PAMI–8, No. 4, Jul. 1986 pp. 413–424.

Kok F. Lai and Roland T.Chin; Deformable Contours: Modeling and Extraction; IEEE Transactions on Pattern Analysis and Machine Intelligence, vol. 17, No. 11, pp. 1084–1090.

D. Onnasch, P.H. Heintzen; A Versatile Program for the Documentation and Comparison of Traced Heart Contours; Computers in Cardiology, Long Beach California, IEEE Computer Society, 1975, pp. 257–262.

Richard O. Duda and Peter E. Hart; Use of the Hough Transformation To Detect Lines and Curves in Pictures; Graphics and Image Processing; Communications of the ACM; Jan. 1972 vol. 15 No. 1 pp. 11–15.

*Primary Examiner*—Carl Layno
(74) *Attorney, Agent, or Firm*—Louis J. Capezzuto

(57) ABSTRACT

A method for mapping electrical activity of a heart includes inserting a probe into a chamber of the heart, the probe including at least one position sensing device and a plurality of non-contact electrodes. Position coordinates of the electrodes are determined relative to an endocardial surface of the chamber, using the at least one position sensing device, and electrical potentials are measured at the determined position coordinates using the electrodes. Electrical potentials are computed at a plurality of points on the endocardial surface, using the measured potentials and the position coordinates, so as to generate a map of electrical activity over the endocardial surface based on the computed potentials.

17 Claims, 5 Drawing Sheets

U.S. PATENT DOCUMENTS

| | | | |
|---|---|---|---|
| 5,546,951 A | 8/1996 | Ben-Haim | 128/702 |
| 5,553,611 A | 9/1996 | Budd et al. | 128/642 |
| 5,582,609 A | 12/1996 | Swanson et al. | 606/39 |
| 5,595,183 A | 1/1997 | Swanson et al. | 128/697 |
| 5,662,108 A | 9/1997 | Budd et al. | 128/642 |
| 5,738,096 A | 4/1998 | Ben-Haim | 128/653.1 |
| 5,836,874 A | 11/1998 | Swanson et al. | 600/374 |
| 5,848,972 A | 12/1998 | Triedman et al. | 600/508 |
| 5,897,529 A | 4/1999 | Ponzi | 604/95 |
| 5,913,820 A | 6/1999 | Bladen et al. | 600/407 |
| 5,938,603 A | 8/1999 | Ponzi | 600/424 |
| 5,964,757 A | 10/1999 | Ponzi | 606/45 |
| 6,063,022 A | 5/2000 | Ben-Haim | 600/41 |

RAPID MAPPING OF ELECTRICAL ACTIVITY IN THE HEART

FIELD OF THE INVENTION

The present invention relates generally to invasive methods for mapping of organs in the body, and specifically to methods for mapping electrical activity in the heart.

BACKGROUND OF THE INVENTION

Cardiac mapping is used to locate aberrant electrical pathways and currents within the heart, as well as diagnosing mechanical and other aspects of cardiac activity. Various methods and devices have been described for mapping the heart. Exemplary methods and devices are described in U.S. Pat. Nos. 5,471,982 and 5,391,199 and in PCT patent publications WO94/06349, WO96/05768 and WO97/24981, whose disclosures are incorporated herein by reference. U.S. Pat. No. 5,391,199, for example, describes a catheter including both electrodes for sensing cardiac electrical activity and miniature coils for determining the position of the catheter relative to an externally-applied magnetic field. Using this catheter a cardiologist can collect data from a set of sampled points within a short period of time, by determining the electrical activity at a plurality of locations and determining the spatial coordinates of the locations.

Methods of creating a three-dimensional map of the heart based on these data are disclosed, for example, in European patent application EP 0 974 936 and in a corresponding U.S. patent application Ser. No. 09/122,137, which is assigned to the assignee of the present patent application, and whose disclosure is incorporated herein by reference. As indicated in these applications, position coordinates (and optionally electrical activity, as well) are initially measured at about 10 to 20 points on the interior surface of the heart. These data points are generally sufficient to generate a preliminary reconstruction or map of the cardiac surface to a satisfactory quality. The preliminary map is preferably combined with data taken at additional points in order to generate a more comprehensive map. In clinical settings, it is not uncommon to acquire data at 100 or more sites to generate a detailed, comprehensive map of heart chamber electrical activity.

In order to speed up the process of data acquisition, multiple-electrode catheters have been developed to simultaneously measure electrical activity at multiple points in the heart chamber. Such catheters are described, for example, in U.S. Pat. Nos. 5,487,391 and 5,848,972, whose disclosures are incorporated herein by reference. These catheters having multiple electrodes on a three-dimensional structure, which expands inside the heart to take the form of a basket. The basket structure is designed so that when deployed, its electrodes are held in intimate contact against the endocardial surface. A problem with the catheters disclosed in these patents is that they are both difficult and expensive to produce. The large number of electrodes in such catheters is also very demanding of the data recording and processing subsystem. There are additional complexities associated with the deployment and withdrawal of these catheters, and increased danger of coagulation.

U.S. Pat. No. 4,649,924, whose disclosure is likewise incorporated herein by reference, discloses a non-contact method for the detection of intracardiac electrical potential fields. A catheter having an inflatable distal end portion is provided with a series of sensor electrodes distributed over its surface and connected to insulated electrical conductors for connection to signal sensing and processing means. The size and shape of the end portion are such that the electrodes are spaced substantially away from the wall of the cardiac chamber. The sensor electrodes are preferably distributed on a series of circumferences of the distal end portion, lying in planes spaced from each other. These planes are perpendicular to the major axis of the end portion of the catheter.

PCT patent publication WO99/06112, whose disclosure is also incorporated herein by reference, describes an electrophysiological cardiac mapping system and method based on a non-contact, non-expanded multi-electrode catheter. The electrodes on the catheter are used to simultaneously measure the electrical potentials at multiple points on the catheter surface, inside the volume of the heart chamber. To generate the map, these electrical measurements are combined with a knowledge of the relative geometry of the probe and the endocardium. This geometrical knowledge must be obtained by an independent imaging modality, such as transesophogeal echocardiography. Based on the known geometry, Laplace's equation is solved to find a relation between the potential on the endocardial surface to that on the catheter, in the form of a matrix of coefficients. This matrix is inverted, so as to determine the endocardial potentials based on the electrode potentials. A regularization technique, such as a method of finite element approximation, must be used to ensure proper convergence of the solution.

SUMMARY OF THE INVENTION

It is an object of the present invention to provide an improved method for mapping electrical potentials inside a volume, and particularly on a surface bounding the volume.

It is a further object of some aspects of the present invention to provide an improved method for mapping endocardial electrical potentials.

It is still a further object of some aspects of the present invention to provide a method that enhances the speed with which a map of endocardial electrical potentials can be generated.

It is yet a further object of some aspects of the present invention to provide improved methods and apparatus for mapping electrical potentials in the heart while minimizing contact with the endocardium.

In preferred embodiments of the present invention, a mapping probe, preferably a catheter, is inserted into a chamber of the heart, and is used to generate a map of electrical activity over an endocardial surface of the chamber. The catheter comprises one or more position sensors in a distal portion of the catheter, along with a plurality of electrodes, which are distributed over the surface of the distal portion. A geometrical model of the endocardial surface is formed, preferably using the position-sensing capability of the catheter itself, as described, for example, in the above-mentioned U.S. patent application Ser. No. 09/122,137. Electrical potentials within the volume of the chamber are measured using the electrodes on the catheter surface, whose positions are known precisely due to the position sensors in the catheter. The measured potentials are combined with the geometrical model to generate a map of electrical potentials at the endocardial surface.

Preferably, the map is generated by modeling the electric field in the heart chamber as a superposition of fields generated by discrete electric dipoles distributed over the endocardial surface. In this manner, a set of equations is generated, expressing the potential at each of the points on the catheter as a sum of the dipole fields at that point. The set of equations is inverted to find the strengths of the dipoles on the endocardial surface, from which the activation potentials are then determined. The dipole model has been found to give accurate results, while avoiding the heavy computational burden of finite element approximations and other regularization techniques. Alternatively, however, other methods of computation may be used, such as those described in the above-mentioned PCT publication WO99/06112.

Preferably, the electrodes are distributed over the distal portion of the catheter in an array, most preferably a grid array, as described in a U.S. patent application Ser. No. 09/506,766, which is assigned to the assignee of the present patent application, and whose disclosure is incorporated herein by reference. Further preferably, the catheter comprises two position sensors, one near the distal tip of the catheter, and the other near the proximal end of the electrode array, as described in U.S. Pat. No. 6,063,022, which is also assigned to the assignee of the present patent application, whose disclosure is also incorporated herein by reference. Most preferably, the position sensors comprise miniature coils, which are used to determine position and orientation coordinates by transmitting or receiving electromagnetic waves, as described, for example, in the above-mentioned PCT publication WO96/05768 or U.S. Pat. No. 5,391,199. Alternatively, other types of position sensing systems, as are known in the art, may be used.

The present invention thus achieves the combined benefits of non-contact electrical measurement and rapid mapping. For this reason, it is particularly well suited to mapping of the left ventricle, which must generally be accomplished quickly and with minimal trauma to the heart.

On the other hand, the methods and apparatus of the present invention are also suitable for mapping the other chambers of the heart, as well as for electrical mapping inside other cavities. For instance, the present invention is particularly useful for addressing transient events, as commonly occur in the atria of the heart. One such event is atrial tachycardia, which is a temporary, non-sustained paroxysmal rhythm. A probe in accordance with the present invention can be used to ascertain the effectiveness of therapy used in treating such a disorder. The probe can similarly be used to rapidly confirm the effectiveness of treatment for atrial flutter, for example, to verify that an ablation line or line of blockage is complete and has no gaps.

There is therefore provided, in accordance with a preferred embodiment of the present invention, a method for mapping electrical activity of a heart, including:

inserting a probe into a chamber of the heart, the probe including at least one position sensing device and a plurality of non-contact electrodes;

determining position coordinates of the electrodes relative to an endocardial surface of the chamber, using the at least one position sensing device;

measuring electrical potentials at the determined position coordinates using the electrodes;

computing electrical potentials at a plurality of points on the endocardial surface, using the measured potentials and the position coordinates; and generating a map of electrical activity over the endocardial surface based on the computed potentials.

Preferably, inserting the probe includes positioning the probe such that the non-contact electrodes make substantially no physical contact with the endocardial surface.

Preferably, computing the electrical potentials includes finding an electric dipole strength at each of the plurality of points on the endocardial surface, responsive to the measured potentials. Further preferably, finding the electric dipole strength includes modeling the measured electrical potentials as being due to a superposition of respective electric dipole fields generated at the plurality of points on the endocardial surface, responsive to the determined position coordinates of the electrodes relative to respective position coordinates of the points. Most preferably, finding the electric dipole strength at each of the plurality of points includes deriving a system of equations expressing the measured potentials as a function of the superposition of dipole fields, and inverting the equations.

In a preferred embodiment, computing the electrical potentials includes acquiring a geometrical model of the endocardial surface, and finding a position of each of the electrodes relative to each of the plurality of points on the endocardial surface responsive to the geometrical model. Preferably, acquiring the geometrical model includes using the probe to generate the geometrical model. Most preferably, using the probe to generate the geometrical model includes bringing a distal tip of the probe into contact with a plurality of locations on the endocardial surface so as to determine position coordinates of the locations using the position sensing device, and generating the model using the position coordinates of the locations.

There is also provided, in accordance with a preferred embodiment of the present invention, apparatus for mapping electrical activity of a heart, including:

a probe, having a distal end configured for insertion into a chamber of the heart, the probe including, in proximity to the distal end, at least one position sensing device and a plurality of non-contact electrodes;

a processor, coupled to the probe so as to determine position coordinates of the electrodes relative to an endocardial surface of the chamber, using the at least one position sensing device, and to measure electrical potentials at the determined position coordinates using the electrodes, so as to compute electrical potentials at a plurality of points on the endocardial surface, using the measured potentials and the position coordinates; and a display, coupled to be driven by the processor so as to display a map of electrical activity over the endocardial surface based on the computed potentials.

Preferably, the plurality of non-contact electrodes include an array of electrodes disposed over a surface of the probe in proximity to the distal end, so as to measure the electrical potentials substantially without physical contact with the endocardial surface.

Additionally or alternatively, the at least one is position sensing device includes a first position sensing device adjacent to the distal end of the probe and a second position sensing device in a position proximal to the first position sensing device and in proximity to the array of electrodes.

The present invention will be more fully understood from the following detailed description of the preferred embodiments thereof, taken together with the drawings in which:

DETAILED DESCRIPTION OF PREFERRED EMBODIMENTS

Figure 1:
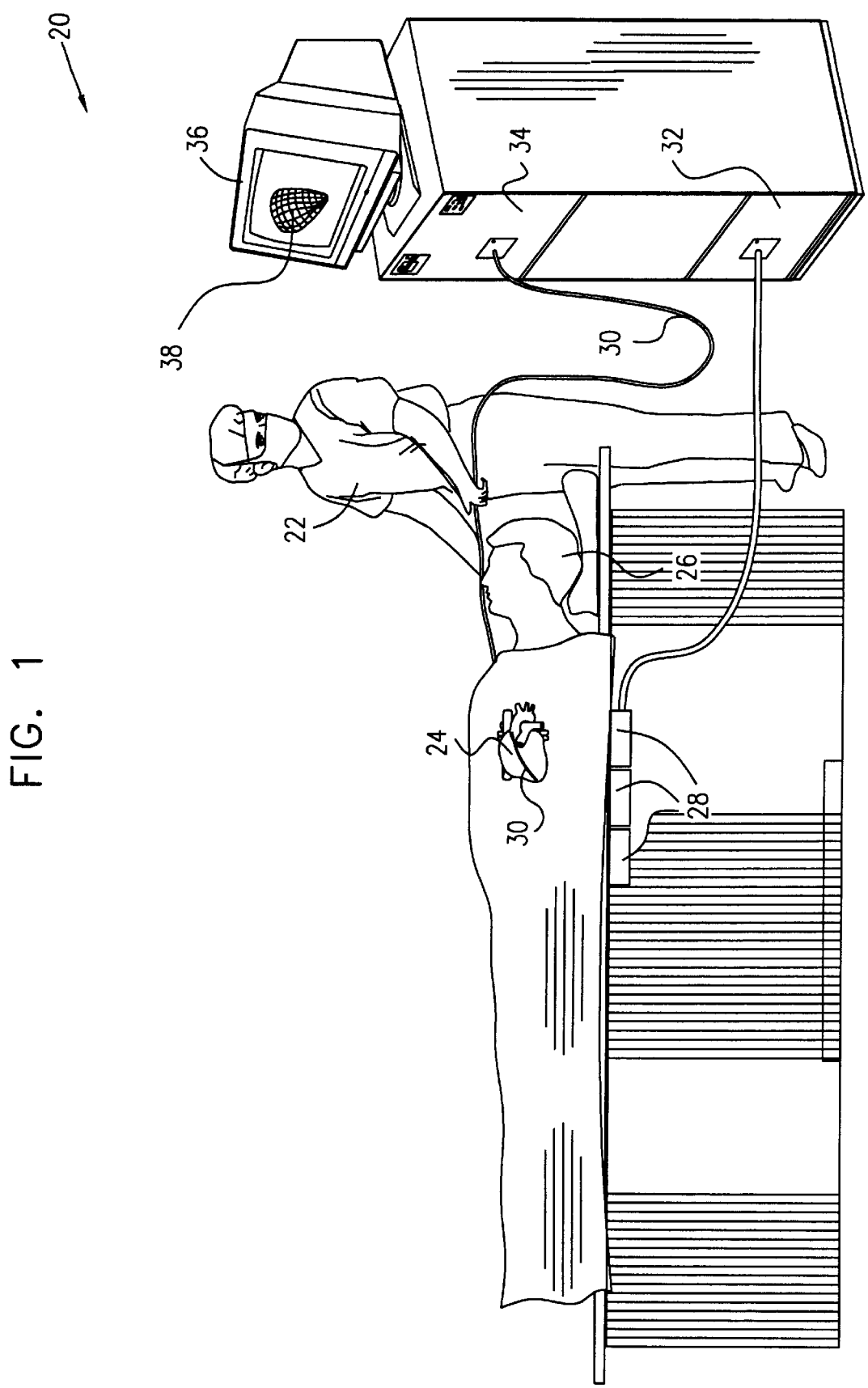
FIG. 1 is a schematic, pictorial illustration of a system for mapping electrical activity in the heart, in accordance with a preferred embodiment of the present invention.

FIG. 1 is a schematic, pictorial illustration of a mapping system 20, for mapping of electrical activity in a heart 24 of a subject 26, in accordance with a preferred embodiment of the present invention. System 20 comprises an elongate probe, preferably a catheter 30, which is inserted by a user 22 through a vein or artery of the subject into a chamber of the heart.

Figure 2:
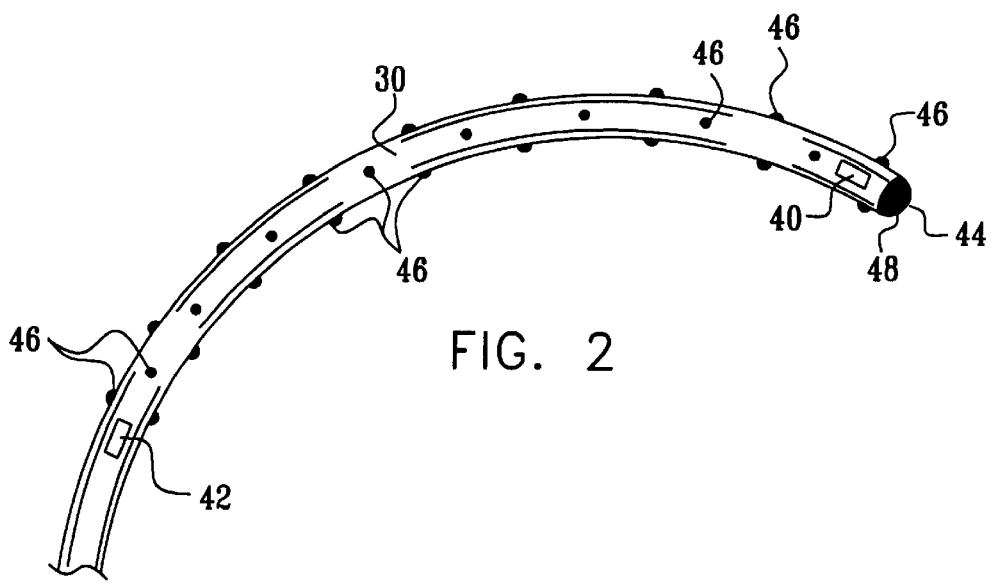
FIG. 2 is a schematic, pictorial illustration of a distal portion of a catheter used in the system of FIG. 1, in accordance with a preferred embodiment of the present invention.
Figure 6:
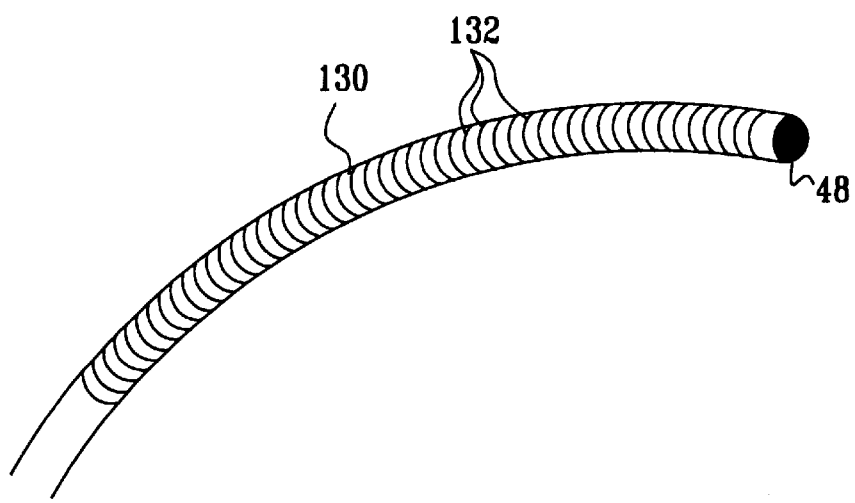
FIG. 6 is a schematic, pictorial illustration of a distal portion of a catheter used in the system of FIG. 1, in accordance with another preferred embodiment of the present invention.
Figure 7:
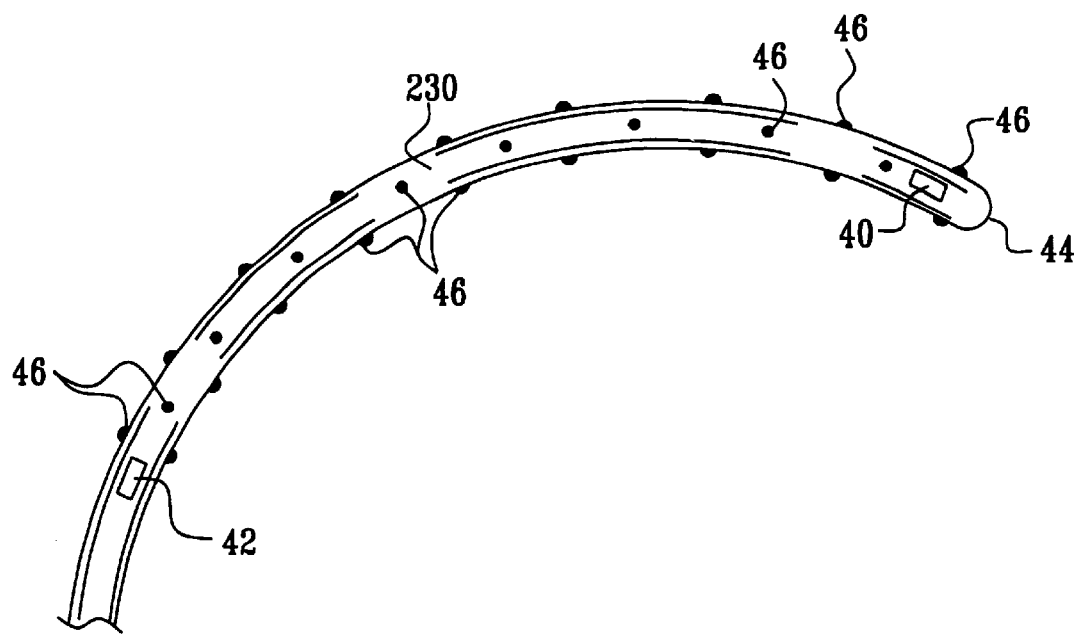
FIG. 7 is a schematic, pictorial illustration of a catheter used in the system of FIG. 1, in accordance with another preferred embodiment of the present invention.

FIGS. 2 and 7 are schematic, pictorial illustrations showing a distal portion of catheter 30, which is inserted into heart 24. The catheter 30 has an array of non-contact electrodes 46 on its outer surface, most preferably in a grid arrangement as shown in the figures. Alternatively, the electrodes may comprise ring electrodes, or substantially any other suitable type of surface electrodes, as shown in FIG. 6. Additionally, the catheter optionally has one or more contact electrodes 48, typically at or near a distal tip 44 of the catheter as shown in FIG. 2.

Catheter 30 also comprises position sensors 40 and 42, preferably one of them near distal tip 44 and the other near a proximal end of the array of electrodes. The sensors preferably comprise electromagnetic sensors, which are mounted within the catheter by any suitable method, for example, using polyurethane glue or the like.

The sensors are electrically connected to an electromagnetic sensor cable (not shown), which extends through the catheter body and into a control handle of the catheter. The electromagnetic sensor cable comprises multiple wires encased within a plastic covered sheath. Within the catheter body, the sensor cable may be enclosed within a protective sheath along with lead wires of electrodes 46 and 48, if desired. In the control handle, the wires of the sensor cable are connected to a circuit board (not shown), which amplifies the signals received from the electromagnetic sensor and transmits them to a computer housed in a console 34 (FIG. 1), in a form understandable to the computer. Also, because the catheter is designed for single use only, the circuit board contains an EPROM chip which shuts down the circuit board after the catheter has been used. This prevents the catheter, or at least the electromagnetic sensor, from being used twice.

A suitable electromagnetic sensor is described, for example, in U.S. Pat. No. 4,391,199, which is incorporated herein by reference. A preferred electromagnetic mapping sensor is manufactured by Biosense Webster (Israel) Ltd., (Tirat Hacarmel, Israel) and marketed under the trade designation NOGA™.

To use the electromagnetic sensor, the patient is placed in a magnetic field generated, for example, by situating under the patient a pad containing field generator coils 28 for generating a magnetic field. A reference electromagnetic sensor (not shown) is preferably fixed relative to the patient, e.g., taped to the patient's back, and catheter 30 containing sensors 40 and 42 is advanced into the patient's heart. Each sensor preferably comprises three small coils which in the magnetic field generate weak electrical signals indicative of their position in the magnetic field. Signals generated by both the fixed reference sensor and sensors 40 and 42 in the heart are amplified and transmitted to console 34, which analyzes the signals and then displays the signals on a monitor 36. By this method, the precise location of the sensors in the catheter relative to the reference sensor can be ascertained and visually displayed. The sensors can also detect displacement of that catheter that is caused is by contraction of the heart muscle.

Some of the features of catheter 30 and system 20 are implemented in the NOGA-STAR™ catheter marketed by Biosense Webster, Inc., and in the above-mentioned Biosense-NOGA system, also marketed by Biosense Webster, Inc.

Further aspects of the design of catheter 30 and of system 20 generally are described in the above-mentioned U.S. patent application Ser. No. 09/506,766. The detailed design of catheter 30 and the electrical mapping functions carried out using the catheter and system 20, however, as described hereinbelow, are unique to the present invention.

Each of sensors 40 and 42 preferably comprises three non-concentric coils, such as those described in the above-mentioned PCT patent publication WO96/05768. The coils sense magnetic fields generated by field generator coils 28, which are driven by driver circuits 32 (FIG. 1). Alternatively, the sensors may generate fields, which are detected by coils 28. System 20 thus achieves continuous generation of six dimensions of position and orientation information with respect to each of sensors 40 and 42. Alternatively, one or both of the sensors may comprise a single coil, which is sufficient, in conjunction with field generator coils 28, to generate three dimensions of position and two dimensions of orientation information. The third dimension of orientation (typically rotation of catheter 30 about its longitudinal axis) can be inferred if needed from a comparison of the coordinates of the two sensors and from mechanical information. Further alternatively, the sensors may comprise other types of position and/or coordinate sensors, as described, for example, in the above-mentioned U.S. Pats. No. 5,391,199, 5,443,489 or PCT publication WO94/04938, or substantially any other suitable type of position/coordinate sensing devices known in the art. Still further alternatively or additionally, catheter 30 is marked with one or more markers whose positions can be determined from outside of the body, such as radio-opaque markers for use with a fluoroscope.

As noted above, catheter 30 is coupled to console 34, which enables the user to observe and regulate the functions of the catheter. Console 34 includes a processor, preferably a computer with appropriate signal processing circuits (which are typically contained inside a housing of the computer). The processor is coupled to drive display 36. The signal processing circuits typically receive, amplify, filter and digitize signals from catheter 30, including signals generated by position sensors 40 and 42 and electrodes 46. The digitized signals are received and used by the console to compute the position and orientation of the catheter and to analyze the electrical signals from the electrodes. The information derived from this analysis is used to generate a map 38 of the heart's electrical activity.

Typically, system 20 includes other elements, which are not shown in the figures for the sake of simplicity. Some of these elements are described in the above-mentioned U.S. patent application Ser. No. 09/122,137. For example, system 20 may include an ECG monitor, coupled to receive signals from one or more body surface electrodes, so as to provide an ECG synchronization signal to console 34. As mentioned above, the system typically also includes a reference position sensor, either on an externally-applied reference patch attached to the exterior of the patient's body, or on an internally-placed catheter, which is inserted into heart 24 and maintained in a fixed position relative to the heart. By comparing the position of catheter 30 to that of the reference catheter, the coordinates of catheter 30 are accurately determined relative to the heart, irrespective of heart motion. Alternatively, any other suitable method may be used to compensate for heart motion.

Figure 3:
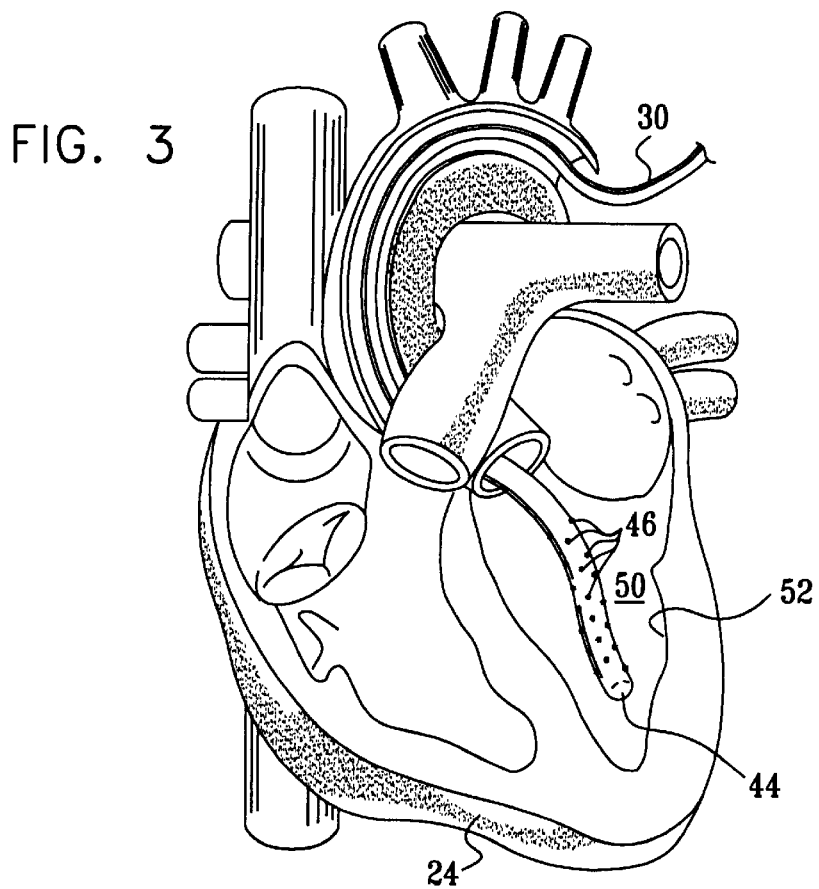
FIG. 3 is a schematic, sectional illustration of a heart into which the catheter of FIG. 2 has been inserted, in accordance with a preferred embodiment of the present invention.

FIG. 3 is a schematic, sectional illustration of heart 24, showing the distal portion of catheter 30 inserted through the aorta into a left ventricle 50 of the heart, in accordance with a preferred embodiment of the present invention. Electrodes 46 receive electrical signals from endocardium 52, responsive to the electric field created in the volume of the ventricle as activation potentials pass through the heart wall.

Tip electrode 48 (FIG. 2), as well as one or more of electrodes 46, may actually come in contact (either partial contact or full contact) with endocardium 52, depending on the unique anatomy of the mapped heart chamber and the configuration of the distal end of catheter 30.

With the embodiment of FIG. 2, it is possible, however, to bring the tip electrode 48 at the tip 44 of the catheter 30 into contact with the endocardium, in order to supplement the "far field" electrical measurements made by electrodes 46 with "near field" measurements at one or more specific points on the endocardium. Using tip electrode 48 in this way also makes it possible to confirm contact of distal tip 44 with the endocardium and to establish a known position or point in the heart chamber. Furthermore, the position-sensing capability of catheter 30 also enables it to be used to generate a geometrical map of ventricle 50, as described hereinbelow.

Figure 4:
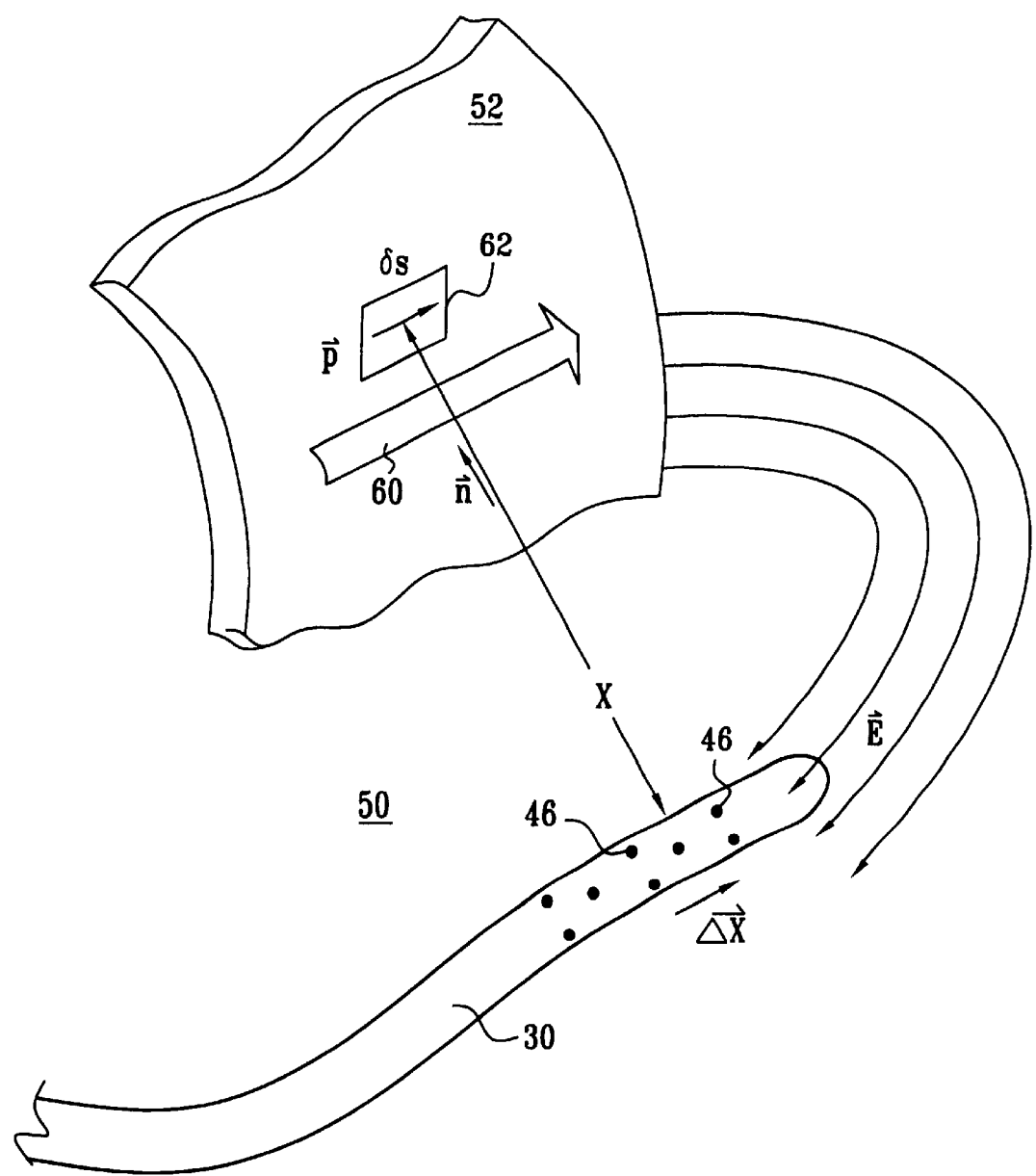
FIG. 4 is a schematic, pictorial illustration showing a detail of the catheter and an endocardial surface in the heart of FIG. 3, useful in understanding a method for mapping electrical activity in the heart, in accordance with a preferred embodiment of the present invention.

FIG. 4 is a schematic, pictorial illustration showing a detail of catheter 30, together with a portion of endocardium 52. The detail is shown here to aid in describing a method for mapping electrical activity in the endocardium, in accordance with a preferred embodiment of the present invention. Activation potentials moving through the endocardium, as indicated by an arrow 60, generate an electric field $\vec{E}$ in ventricle 50. The field causes a potential difference $V_{ij}$ to exist between each pair (i,j) of neighboring electrodes 46 on the catheter surface. For the purpose of the present analysis, the surface of endocardium 52 is broken up into polygonal tiles 62 of arbitrary size $\delta S$, each generating a respective element of the electric field $\vec{E}_k$. For each pair of electrodes 46, having respective position coordinates $X_i$ and $X_j$, which are separated by a vector distance $\Delta \vec{X}$, the potential difference $V_{ij}$ is given by summing over all of tiles 62:

$$V_{ij} = \sum_j \frac{|\vec{E}_k(X_i) - \vec{E}_k(X_j)|}{2} \cdot \Delta \vec{X} \quad (1)$$

Each of tiles 62 can be viewed as a dipole $\vec{p}_k$, corresponding to displacement of charge in endocardium 52 as the activation wave advances. In particular, the peak amplitude of the dipole is proportional to the peak amplitude of the activation potential in the endocardium. The electrical field $\vec{E}_k(X_i)$ due to the dipole is given by:

$$\vec{E}_k = \frac{3\vec{n}_i(\vec{p}_k \cdot \vec{n}_i) - \vec{p}_k}{X_{ik}^3} \quad (2)$$

[following Jackson, *Classical Electrodynamics* (Second Edition, John Wiley & Sons, 1975), page 138]. As illustrated in FIG. 4, $X_{ik}$ is the distance from tile k to electrode i in its current location on catheter 30, and $\vec{n}_i$ is the unit vector pointing from the electrode to the tile.

Figure 5:
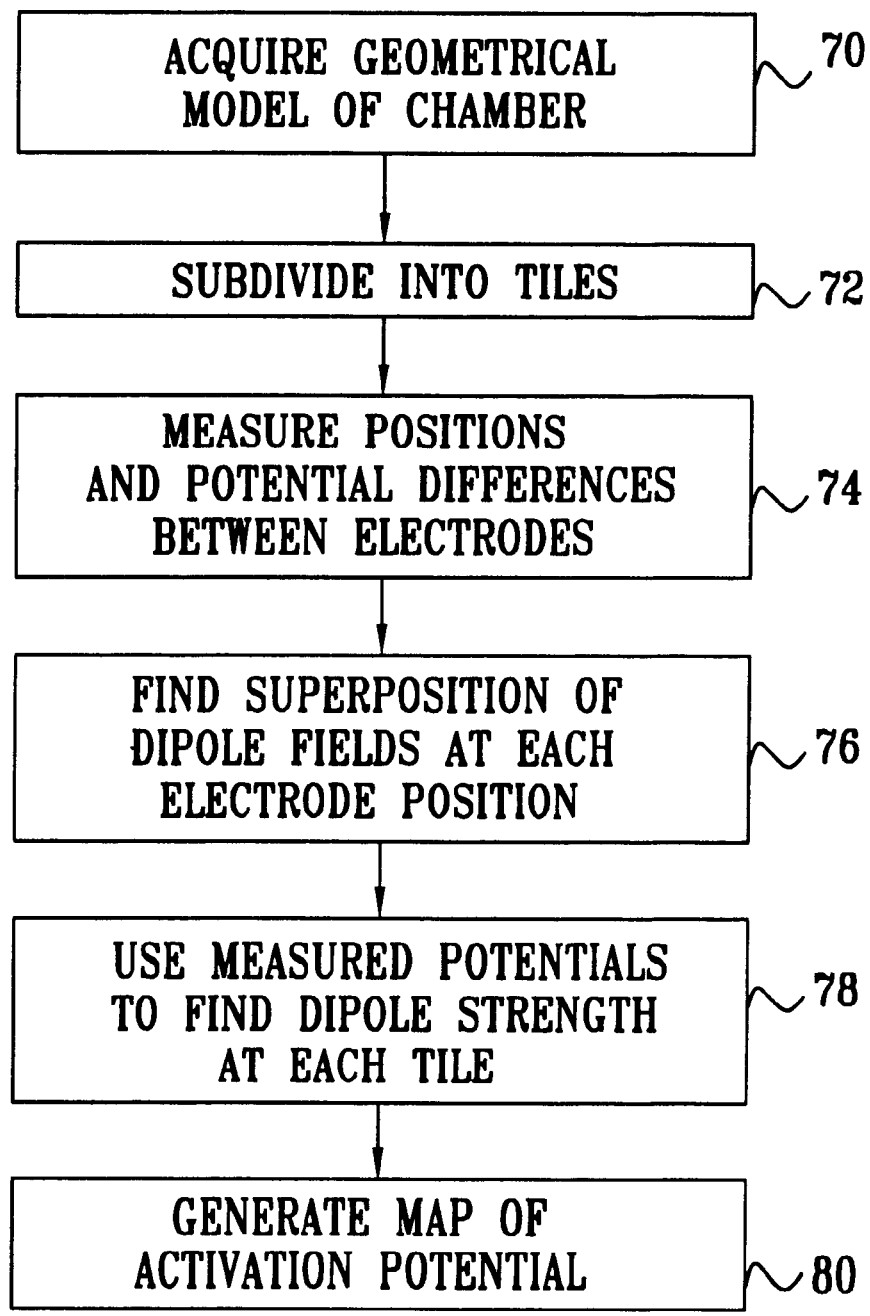
FIG. 5 is a flow chart that schematically illustrates a method for mapping electrical activity in the heart, in accordance with a preferred embodiment of the present invention.

FIG. 5 is a flow chart that schematically illustrates a method for mapping electrical activity in heart 24, using the principles described above, in accordance with a preferred embodiment of the present invention. At a geometrical modeling step 70, a geometrical model or map of ventricle 50 is acquired. Preferably, tip 44 of catheter 30 is brought into contact with a plurality of locations on endocardium 52 of ventricle 50. At each contact location, sensor 40 is used to record the corresponding position coordinates. Optionally, the surface electrical activity is measured at each of these points, as well, for later reference. The coordinates taken at the plurality of locations are used for producing a geometrical map of heart 24, as described in the above-mentioned U.S. patent application Ser. No. 09/122,137. Alternatively, an image of the heart, such as an ultrasound image, or another method of mapping may be used to provide the geometrical map, without necessarily using catheter 30.

The surface of endocardium 52 is divided into tiles 62, at a tiling step 72. At a measurement step 74, the potential differences between all pairs of neighboring electrodes 46 on catheter 30 are determined. At the same time, the positions of all of the electrodes are determined, using sensors 40 and 42. The position and potential measurements are preferably all made at the same, known time, most preferably at a given, fixed time relative to the cardiac cycle of heart 24. Further preferably, the position and potential measurements are repeated several times, at different locations in ventricle 50. Optionally, measurements are made at each of a number of different times in the cardiac cycle, so that the electrical activity in the endocardium can be mapped in different phases of the cycle. In this case, the geometrical model acquired at step 70 is preferably a dynamic model, which is adjusted for motion of endocardium 52 during the heart cycle.

The position measurements are used in a straightforward geometric manner to determine the values of $X_i$, $X_j$, $\Delta \vec{X}$, $X_{ik}$ and $\vec{n}_i$ in equations (1) and (2) for all of electrodes 46 and tiles 62, at a superposition step 76. As a result, the field (or potential) at each electrode measurement position is expressed as a function of the unknown dipole strengths $\vec{p}_k$. In other words, the measurements made at step 74 provide the values of all of the variables in equations (1) and (2), with the exception of the individual dipole strengths $\vec{p}_k$. Alternatively, each of tiles 62 may be modeled as an equipotential surface, with appropriate changes to equation (2).

To calculate the dipole strengths, the equations found at step 76 are inverted, at a dipole determination step 78. As long as the number of tiles is no greater than the number of measurement points, the dipole strengths of all of the tiles are fully determined. Preferably, however, position and potential measurements are made at a number of points that is substantially larger than the number of tiles. A statistical averaging procedure, as is known in the art, is applied to the measurement results in order to remove outliers and reduce error. Thus, the greater the number of measurement points, the more accurately are the dipole strengths determined. The determined dipole strengths (or alternatively, the potentials) are used at a mapping step 80 to generate map 38, showing the activation potentials over the entire endocardium 52 of ventricle 50. The map may present the potentials in substantially any form known in the art, such as a three-dimensional graph of equipotential lines, isochronal lines or peak potentials, or a two-dimensional projection of the heart wall showing these or other aspects of the electrical activity. Variations on these methods of mapping and data visualization will be apparent to those skilled in the art.

FIG. 6 is a schematic, pictorial illustration showing a distal portion of a catheter 130, in accordance with another preferred embodiment of the present invention. Catheter 130 is substantially similar in construction and use to catheter 30, described in detail hereinabove, except that instead of point electrodes 46, catheter 130 has an array of ring electrodes 132. In one exemplary embodiment, the catheter has thirty-two ring electrodes, spaced approximately 0.5 mm apart.

Although the preferred embodiment described above relates to mapping of left ventricle 50, the extension of the methods of the present invention to the other chambers of the heart is straightforward. Those skilled in the art will also recognize that the principles of the present invention may be applied to mapping of other organs and cavities, as well. It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for mapping electrical activity of a heart, comprising:
    inserting a probe into a chamber of the heart, the probe comprising at least one position sensing device and a plurality of non-contact electrodes;
    determining position coordinates of the electrodes relative to an endocardial surface of the chamber, using the at least one position sensing device;
    measuring electrical potentials at the determined position coordinates using the electrodes;
    computing electrical potentials at a plurality of points on the endocardial surface, using the measured potentials and the position coordinates by finding an electric dipole strength at each of the plurality of points on the endocardial surface, responsive to the measured potentials; and
    generating a map of electrical activity over the endocardial surface based on the computed potentials.

2. A method according to claim 1, wherein inserting the probe comprises positioning the probe such that the non-contact electrodes make substantially no physical contact with the endocardial surface.

3. A method according to claim 2, wherein finding the electric dipole strength comprises modeling the measured electrical potentials as being due to a superposition of respective electric dipole fields generated at the plurality of points on the endocardial surface, responsive to the determined position coordinates of the electrodes relative to respective position coordinates of the points.

4. A method according to claim 3, wherein finding the electric dipole strength at each of the plurality of points comprises deriving a system of equations expressing the measured potentials as a function of the superposition of dipole fields, and inverting the equations.

5. A method according to claim 1, wherein computing the electrical potentials comprises acquiring a geometrical model of the endocardial surface, and finding a position of each of the electrodes relative to each of the plurality of points on the endocardial surface responsive to the geometrical model.

6. A method according to claim 5, wherein acquiring the geometrical model comprises using the probe to generate the geometrical model.

7. A method according to claim 6, wherein using the probe to generate the geometrical model comprises bringing a distal tip of the probe into contact with a plurality of locations on the endocardial surface so as to determine position coordinates of the locations using the position sensing device, and generating the model using the position coordinates of the locations.

8. Apparatus for mapping electrical activity of a heart, comprising:
    a probe, having a distal end configured for insertion into a chamber of the heart, the probe comprising, in proximity to the distal end, at least one position sensing device and a plurality of non-contact electrodes;
    a processor, coupled to the probe so as to determine position coordinates of the electrodes relative to an endocardial surface of the chamber, using the at least one position sensing device, and to measure electrical potentials at the determined position coordinates using the electrodes, so as to compute electrical potentials at a plurality of points on the endocardial surface, using the measured potentials and the position coordinates, wherein the processor is adapted to compute an electric dipole strength at each of the plurality of points, responsive to the measured potentials; and
    a display, coupled to be driven by the processor so as to display a map of electrical activity over the endocardial surface based on the computed potentials.

9. Apparatus according to claim 8, wherein the plurality of non-contact electrodes comprise an array of electrodes disposed over a surface of the probe in proximity to the distal end, so as to measure the electrical potentials substantially without physical contact with the endocardial surface.

10. Apparatus according to claim 9, wherein the at least one position sensing device comprises a first position sensing device adjacent to the distal end of the probe and a second position sensing device in a position proximal to the first position sensing device and in proximity to the array of electrodes.

11. Apparatus according to claim 8, wherein the processor is adapted to model the measured electrical potentials as being due to a superposition of respective electric dipole fields generated at the plurality of points, responsive to the determined position coordinates of the electrodes relative to respective position coordinates of the points.

12. Apparatus according to claim 11, wherein the processor is adapted to find a system of equations expressing the measured potentials as a function of the superposition of dipole fields, and to compute the electric dipole strengths by inverting the equations.

13. Apparatus according to claim 8, wherein the processor is adapted to acquire a geometrical model of the endocardial surface, and to find a position of each of the electrodes relative to each of the plurality of points on the endocardial surface responsive to the geometrical model.

14. Apparatus according to claim 13, wherein the processor is adapted to generate the geometrical model using the probe.

15. Apparatus according to claim 14, wherein to generate the geometrical model, the distal end of the probe is brought into contact with a plurality of locations on the endocardial surface so as to determine position coordinates of the locations using the position sensing device, and wherein the processor is adapted to generate the model using the position coordinates of the locations.

16. Apparatus according to claim 8, including at least one contact electrode on the distal end of the catheter.

17. Apparatus according to claim 9, wherein the non-contact electrodes are ring electrodes.

* * * * *

UNITED STATES PATENT AND TRADEMARK OFFICE
CERTIFICATE OF CORRECTION

PATENT NO. : 6,400,981 B1
DATED : June 4, 2002
INVENTOR(S) : Assaf Govari

It is certified that error appears in the above-identified patent and that said Letters Patent is hereby corrected as shown below:

<u>Column 7,</u>
Lines 60-65,

" $$V_{ij} = \sum_j \frac{|\bar{E}_t(x_i) - \bar{E}_t(x_j)|}{2} \bullet \Delta \bar{X}$$ "

should be
--
$$V_{ij} = \sum_k \frac{|\bar{E}_t(x_i) - \bar{E}_t(x_j)|}{2} \bullet \Delta \bar{X}$$
--

Signed and Sealed this

Thirtieth Day of March, 2004

JON W. DUDAS
*Acting Director of the United States Patent and Trademark Office*